(12) United States Patent
Owen

(10) Patent No.: US 6,241,945 B1
(45) Date of Patent: Jun. 5, 2001

(54) MODULAR COMBINED PUMP, FILTRATION, OXYGENATION AND/OR DEBUBBLER APPARATUS

(75) Inventor: Donald R. Owen, New Orleans, LA (US)

(73) Assignee: Life Science Holdings, Inc., Des Plaines, IL (US)

(*) Notice: Subject to any disclaimer, the term of this patent is extended or adjusted under 35 U.S.C. 154(b) by 0 days.

(21) Appl. No.: 09/039,318

(22) Filed: Mar. 16, 1998

(51) Int. Cl.⁷ ..................................................... A61M 1/14
(52) U.S. Cl. ................... 422/44; 422/45; 422/48; 604/4.01; 604/6.09; 604/6.11; 604/6.14; 210/252; 210/257.2; 210/260; 210/261; 210/322; 210/337; 210/335
(58) Field of Search .................. 422/44–48; 604/4–6; 210/650–53, 182–85, 258–61, 252–53, 255, 256, 257.1–257.2, 322–323.1, 335, 337–44

(56) References Cited

U.S. PATENT DOCUMENTS

| | | |
|---|---|---|
| 3,839,204 * | 10/1974 | Ingenito et al. ..................... 210/321 |
| 4,183,961 | 1/1980 | Curtis . |
| 4,371,438 | 2/1983 | Benattar et al. . |
| 4,422,939 * | 12/1983 | Sharp et al. ......................... 210/445 |
| 4,597,868 | 7/1986 | Watanabe . |
| 4,668,394 * | 5/1987 | Badolato et al. .................... 210/314 |
| 5,015,388 * | 5/1991 | Pusineri et al. ..................... 210/641 |
| 5,158,533 | 10/1992 | Strauss et al. . |
| 5,162,101 * | 11/1992 | Cosentino et al. .................... 422/46 |
| 5,270,005 | 12/1993 | Raible . |
| 5,514,335 * | 5/1996 | Leonard et al. ....................... 422/46 |
| 5,634,892 | 6/1997 | Whalen . |

FOREIGN PATENT DOCUMENTS 221 361 A1   4/1985  (DE) .
0 324 919 A2  7/1989  (EP) .

* cited by examiner

Primary Examiner—Angela D. Sykes
Assistant Examiner—Patricia Bianco
(74) Attorney, Agent, or Firm—Oliff & Berridge, PLC

(57) ABSTRACT

A customized pump, filtration, oxygenation and/or debubbler apparatus includes a first pump module, a filtration module, an oxygenation module, a debubbler module and/or a second pump module. Each module is formed of stackable support members with filtration, oxygenation and/or degassing membranes interposed therebetween.

26 Claims, 3 Drawing Sheets

MODULAR COMBINED PUMP, FILTRATION, OXYGENATION AND/OR DEBUBBLER APPARATUS

BACKGROUND OF THE INVENTION

1. Field of Invention

The invention relates to modules stackable to form a customized combined pump, filtration, oxygenation and/or debubbler apparatus. Such apparatus may be used, for example, in an apparatus that delivers fluid to and/or circulates medical fluid through a mammal.

2. Description of Related Art

Apparatus that deliver to and/or circulate fluid through a mammal often require that the fluid be oxygenated, filtered and/or debubbled depending on the specific utilization of the apparatus. Further, some type of pump is generally also required for pushing or pulling the fluid through the apparatus. For example, extracorporeal circulation of blood may require oxygenation, filtration and/or debubbling of the blood as well as some type of pump if the blood is to be reintroduced into a mammal.

Oxygenation involves placing a fluid, such as, for example, blood, in close enough proximity to oxygen so that the oxygen is absorbed by and may react with the fluid. This can be accomplished by passing the fluid along, for example, one side of an oxygenation membrane supplied with oxygen on the other side. Filtration involves passing fluid through a porous substance, for example, a filtration membrane, that prevents particles larger than a certain size from passing through. This allows undesirable components within the fluid to be removed. Debubbling involves removing gas bubbles from a liquid. For example, where a fluid has been oxygenated, extraneous air or oxygen bubbles may remain in the fluid. These bubbles may be removed by passing the fluid along, for example, a gas permeable/liquid impermeable membrane or degassing membrane, and withdrawing the extraneous gas therethrough. Apparatus for oxygenating, filtering and/or debubbling a fluid prior to delivering to and/or circulating fluid through a mammal are known. Known apparatus, however, are large and bulky. Further, these known apparatus are generally designed as integrated, unitary apparatus with desired components integrated into the unitary apparatus. See, for example, U.S. Pat. No. 5,634,892, which discloses an integrated pump/oxygenator apparatus designed for cardiopulmonary support formed of a two stage pump system combined with a membrane oxygenator enclosed within a housing;

U.S. Pat. No. 5,514,335, which discloses a cardiotomylvenous blood reservoir with a defoaming and filtering chamber integrated with an oxygenator, heat exchanger device and pump; U.S. Pat. No. 5,270,005, which discloses an integrated blood reservoir/oxygenator/heat exchange/pump apparatus; U.S. Pat. No. 5,158,533, which discloses a combined cardiotomy/venous reservoir/pleural drainage unit having integrated therein pump means and apparatus for filtering and defoarming blood; and U.S. Pat. No. 4,138,961, which discloses an integrated oxygenator/defoamer apparatus designed for extracorporeal circulation.

SUMMARY OF THE INVENTION

The present invention provides modules stackable to form a combined pump, filtration, oxygenation and/or debubbler apparatus. The combined apparatus is capable of pumping a fluid through a system as well as oxygenating, filtering and/or debubbling the fluid. Because the modules are each formed of a plurality of stackable support members, the modules are easily combinable to form a compact apparatus containing desired components. Filtration, oxygenation and/or degassing membranes are disposed between the support members.

The invention is particularly applicable in a portable apparatus capable of delivering to and/or circulating a fluid through a mammal where minimizing the size and/or weight of the apparatus is highly desirable, for example to provide ready portability and applicability to field use. Further, because the components are modular, undesired components may be removed, or the components may be rearranged to create a customized apparatus, with desired oxygenation, filtration and/or degassing membranes interposed between the support members.

BRIEF DESCRIPTION OF THE DRAWINGS

These and other aspects and advantages of the invention will become apparent from the following detailed description of embodiments when taken in conjunction with the accompanying drawings, in which.

DETAILED DESCRIPTION OF PREFERRED EMBODIMENTS

Figure 1:
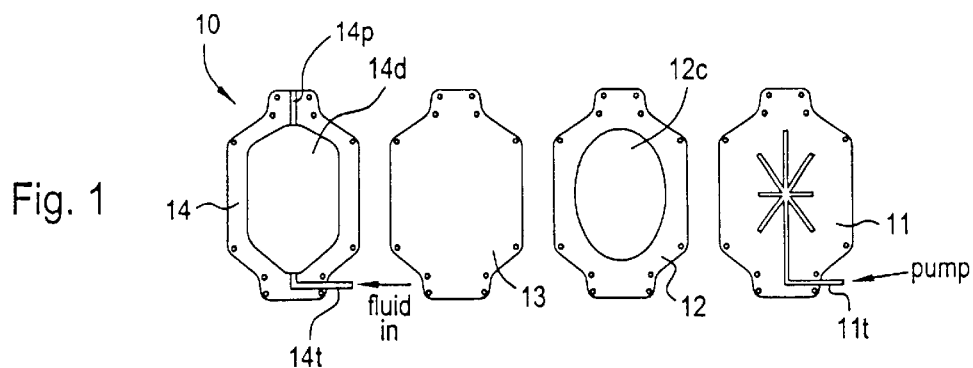
FIG. 1 is an exploded view of a first pump module according to the invention.
Figure 2:
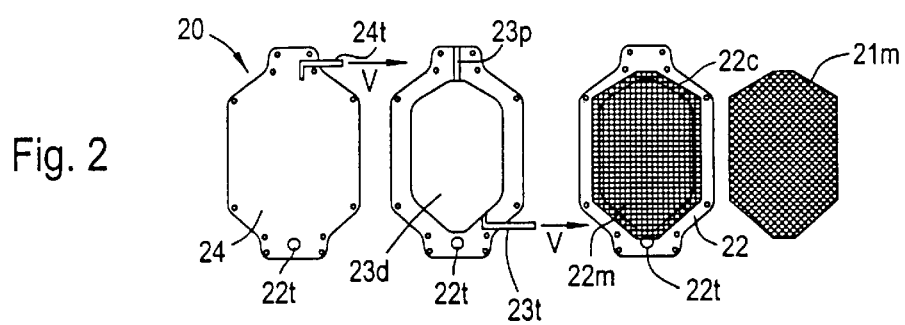
FIG. 2 is an exploded view of a filtration module according to the invention.
Figure 3:
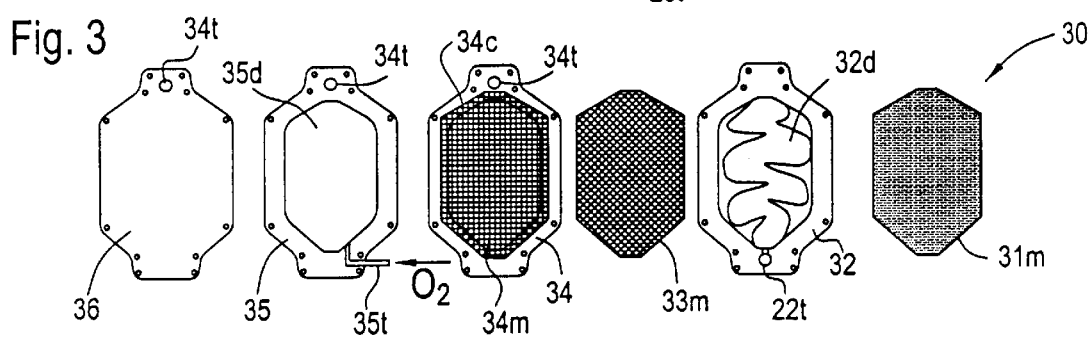
FIG. 3 is an exploded view of an oxygenation module according to the invention.
Figure 4:
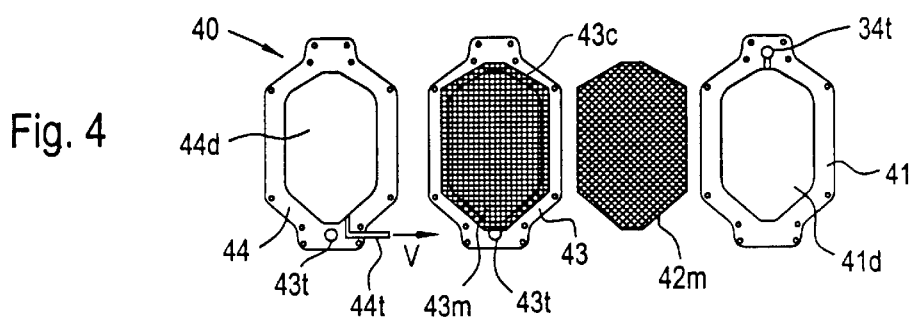
FIG. 4 is an exploded view of a debubbler module according to the invention.
Figure 5:
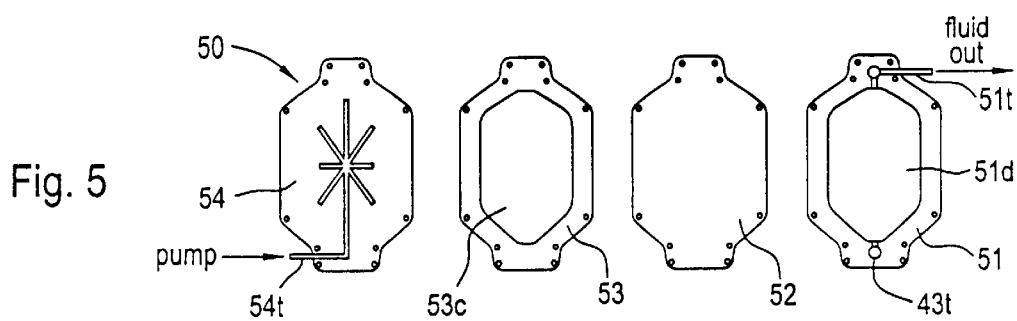
FIG. 5 is an exploded view of a second pump module according to the invention.

For a general understanding of the features of the invention, reference is made to the drawings. In the drawings, like reference numerals have been used throughout to designate like elements.

Figure 6:
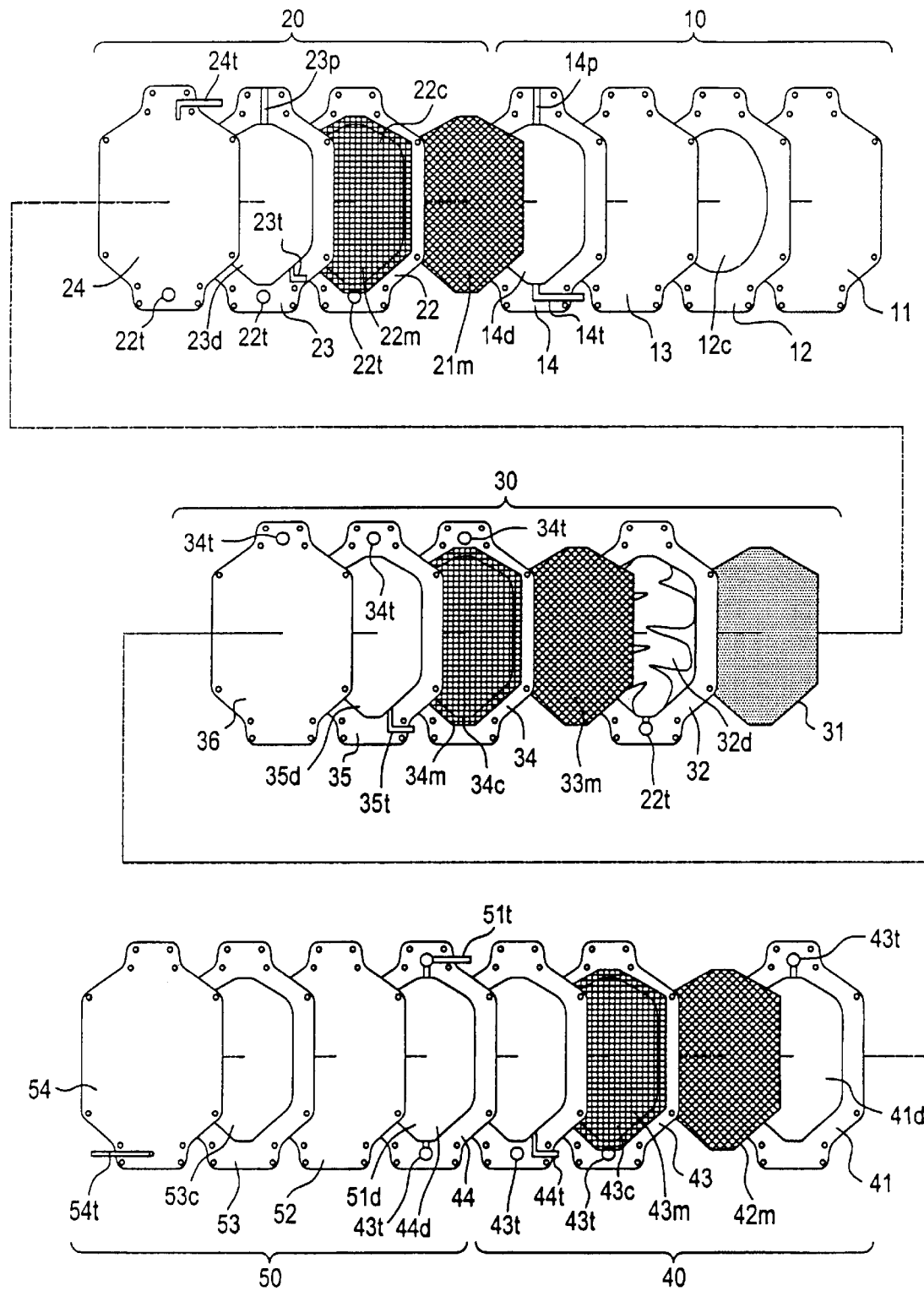
FIG. 6 is an exploded perspective view showing the modules of FIGS. 1-5 assembled together.
Figure 7:
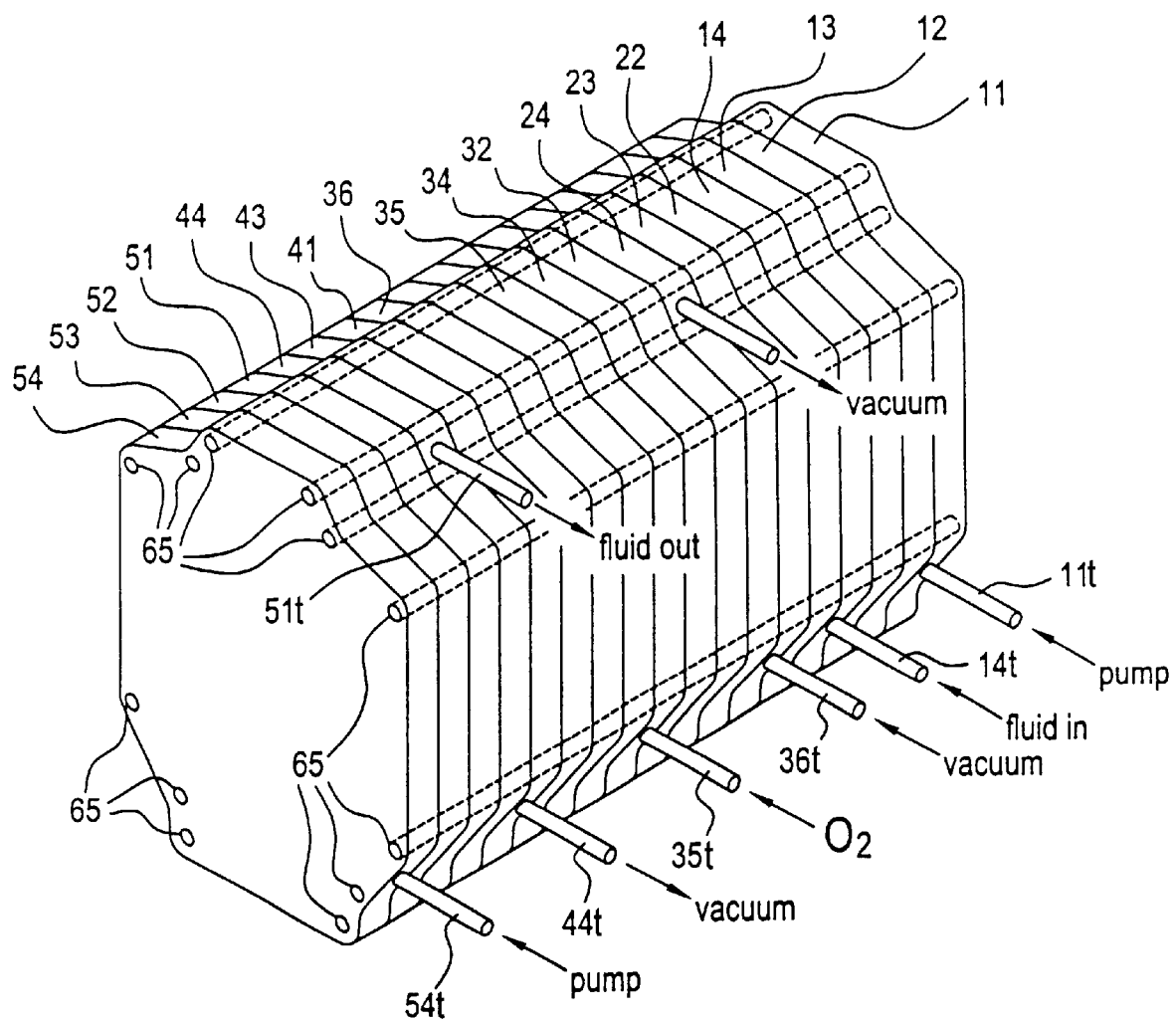
FIG. 7 is a front perspective view of an assembled apparatus according to the invention.

FIGS. 1–5 show various modules that may be stacked to form a combined pump, filtration, oxygenation and/or debubbler apparatus, such as the combined pump, filtration, oxygenation and debubbler apparatus 1 shown in FIGS. 6–7. As depicted in these figures, the combined pump, filtration, oxygenation and debubbler apparatus 1 is preferably formed of a plurality of stackable support members groupable to form one or more modules.

Interposed between the plurality of stackable support member are filtration, oxygenation and/or degassing membranes depending on a particular user's needs. The filtration, oxygenation and/or degassing membranes are preferably commercially available macro-reticular hydrophobic polymer membranes hydrophilically grafted in a commercially known way, such as, for example, ethoxylation, to prevent protein deprivation, enhance biocompatibility with, for example, blood and to reduce clotting tendencies. The filtration membrane(s) is preferably hydrophilically grafted all the way through and preferably has a porosity (pore size) within a range of 15 to 35$\mu$, more preferably 20 to 30$\mu$, to filter debris in a fluid, preferably without filtering out cellular or molecular components of the fluid. The degassing membrane(s) and oxygenation membrane(s) are hydrophilically surface treated to maintain a liquid-gas boundary. The degassing membrane(s) and oxygenation membrane(s) preferably have a porosity of 15 μ or less, more preferably 10 μ or less. The modules may include a first pump module 10, as shown in exploded view in FIG. 1; a filtration module 20, as shown in exploded view in FIG. 2; an oxygenation module 30, as shown in exploded view in FIG. 3; a debubbler module 40, as shown in exploded view in FIG. 4; and a second pump module 50, as shown in exploded view in FIG. 5. The pump modules are each connected to a source of pump fluid and are actuated either manually or by a controller of the device in which the apparatus is employed. The support members are preferably similarly shaped. For example, the support members may each be plate-shaped; however, other shapes may also be appropriate. As shown in FIG. 7, the support members are preferably removably connected by screws or bolts 65; however, other fasteners for assembling the apparatus may also be appropriate.

The first pump module 10 preferably includes a first (end) support member 11, a second support member 12 with a cut-out center area 12c, a diaphragm 13 and a third support member 14. The support members of this module and each of the other modules are preferably thin and substantially flat (plate-like), and can be formed of any appropriate material with adequate rigidity and preferably also biocompatibility. For example, various resins and metals may be acceptable. A preferred material is an acrylic/polycarbonate resin.

The first (end) support member 11 is preferably solid and provides support for the pump module 10. The first (end) support member 11 preferably includes a domed-out, i.e concave cavity for receiving pump fluid such as air. Tubing 1 lt is provided to allow the pump fluid to enter the pump module 10. The diaphragm 13 may be made of any suitable elastic and preferably biocompatible material, and is preferably polyurethane. The third support member 14 includes a domed-out fluid cavity 14d and tubing 14t for receiving fluid, such as, for example, blood or an artificial perfusate, into the cavity 14d of the pump module 10. The first pump module, or any of the other modules, may also include a port 14p for sensors or the like. Preferably hemocompatible anti-backflow valves serve to allow unidirectional flow through the pump module 10.

The filtration module 20 preferably includes a filtration membrane 21m which forms a boundary of cavity 14d, a first support member 22 with a cut-out center area 22c, a degassing membrane 22m and second and third support members 23 and 24. The filtration membrane 21m is preferably a 25 macro-reticular filtration membrane modified to enhance biocompatibility with, for example, blood and to reduce clotting tendencies (like the other supports, filters and membranes in the device). The degassing membrane 22m is preferably a 0.2–3 μ macro-reticular degassing membrane with a reverse flow aqueous pressure differential of at least 100 mmHg for $CO_2$ removal surface modified to enhance biocompatibility.

The first support member 22 includes tubing 22t for forwarding fluid into the oxygenation module 30, or another adjacent module, if applicable, after it has passed through the filtration membrane 21m and along the degassing membrane 22m. The second support member 23 of the filtration module 20 includes a domed-out cavity 23d and tubing 23t through which a vacuum may be applied to the cavity 23d to draw gas out of the fluid through the degassing membrane 22m. The third support member 24 is preferably solid and provides support for the filtration module 20. The third support member can also include tubing 24t through which a vacuum may be applied to draw gas out of the fluid through the degassing membrane 31m of the oxygenation module 30 as discussed below. The filtration module 20, or any of the other modules, may also include a port 23p for sensors or the like.

The oxygenation module 30 includes the degassing membrane 31m, a first support member 32, a filtration membrane 33m, an oxygenation membrane 34m, a second support member 34 with a cut-out center area 34c, and third and fourth support members 35, 36. The degassing membrane 31m is preferably a 0.2–3 μ macro-reticular degassing membrane with a reverse flow aqueous pressure differential of at least 100 mmHg surface modified to enhance biocompatibility.

The first support member 32 includes a domed-out fluid cavity 32d. The surface of the domed-out fluid cavity 32d preferably forms a tortuous path for the fluid, which enhances the oxygenation and degassing of the fluid. The filtration membrane 33m is preferably a 25 μ macro-reticular filtration membrane modified to enhance biocompatibility. The oxygenation membrane 34m is preferably a 0.2–1 μ macro-reticular oxygenation membrane with a reverse flow aqueous pressure differential of at least 100 mmHg surface modified to enhance biocompatibility.

The second support member 34 includes tubing 34t for forwarding fluid out of the oxygenation module 30 into the debubbler module 40, or another adjacent module, if applicable, after it has passed through the filtration membrane 33m and along the oxygenation membrane 34m. The third support member 35 includes a domed-out cavity 35d and tubing 35t for receiving oxygen from an external source. The fourth support member 36 is preferably solid and provides support for the oxygenation module 30.

The debubbler module 40 includes a first support member 41, a filtration membrane 42m, a degassing membrane 43m, a second support member 43 having a cut-out center area 43c, and a third support member 44. The first support member 41 has a domed-out fluid cavity 41d.

The filtration membrane 42m is preferably a 25 μ a macro-reticular filtration membrane modified to enhance biocompatibility. The degassing membrane 43m is preferably a 0.2–3 μ macro-reticular degassing membrane with a reverse flow aqueous pressure differential of at least 100 mmHg surface modified to enhance biocompatibility. The second support member 43 has tubing 43t for forwarding fluid out of the debubbler module 40 into the pump module 50, or another adjacent module, if applicable, after the fluid had passed through the filtration membrane 42m and along the degassing membrane 43m. The third support member 44 includes a domed-out cavity 44d and tubing 44t through which a vacuum may be applied to draw gas out of the fluid through the degassing membrane 43m.

The second pump module 50 may correspond to the first pump module 10. It preferably includes a first support member 51, a diaphragm 52, a second support member 53 with a cut-out center area 53c, and a third (end) support member 54. The first support member 51 includes a domed out fluid cavity 51d and tubing 51t for allowing fluid to exit the pump module. The diaphragm 52 is preferably a polyurethane bladder.

The third (end) support piece member 54 is preferably solid and provides support for the pump module 10. Support member 54 preferably includes a domed out cavity (not shown) for receiving pump fluid. Tubing 54a is provided to allow the pump fluid such as air to enter the pump module 50. Preferably hemocompatible anti-backflow valves may serve to allow unidirectional flow through the pump module 50.

In operation, fluid enters the first pump module 10 through tube 14t, passes through the filtration membrane 21m into the filtration module 20 and along the degassing membrane 22m. A small vacuum force is applied through tubing 23t to draw gas out of the fluid through the degassing membrane 22m. Next, the fluid travels into the oxygenation module 30 via internal tubing 22t, passing along the degassing membrane 31m, through the filtration membrane 33m and along the oxygenation membrane 34m. A small vacuum force is applied through tubing 24t to draw gas out of the fluid through the degassing membranes 31m. Oxygen is received into the domed-out cavity 35d of the third support member of the oxygenation module 30 via tubing 35t and passes through the oxygenation membrane 34m into the fluid as the fluid travels along its surface.

After being oxygenated by the oxygenation module 30, the fluid then travels via internal tubing 34t into the debubbler module 40. The fluid passes through the filtration membrane 42m and along the degassing membrane 43m. A small vacuum force is applied through tubing 44t to draw gas out of the fluid through the degassing membrane 43m. After passing through the degassing module 40, the fluid travels into the second pump module 50 through tubing 41t, and exits the second pump module 50 via tubing 51t.

The combined pump, filtration, oxygenation and debubbler apparatus according to the invention allows the minimization of dead volume and polymer to blood contact. Gaseous polymer grafting technology allows the hemocompatibility of this device to be achieved in a single step.

Any suitable pumping device, for example, a pulsatile or rotary, pneumatically, hydraulically or electrically actuated device with appropriate valves may replace the pump modules 10, 50 discussed above. Alternatively, the filtration, oxygenation and debubbler modules 20, 30 and 40 previously described may be used without the pump modules 10, 50, or in various combinations.

The above described apparatus can be utilized with any device which requires pumping, filtering, oxygenating and/or degassing of a fluid, such as, for example, a brain resuscitation device, such as that disclosed in simultaneously filed co-pending application Ser. No. 09/039,537, which is hereby incorporated by reference; an organ perfusion device; an extra-corporeal pulmonary support device; or the like. The apparatus is particularly useful in such devices designed to be portable or for field use, where minimizing the size and/or weight of apparatus is highly desirable.

While the invention has been described in conjunction with a specific embodiment thereof, it is evident that many alternatives, modifications and variations may be apparent to those skilled in the art. Accordingly, the preferred embodiment of the invention as set forth herein is intended to be illustrative, not limiting. Various changes may be made without departing from the spirit and scope of the invention as defined in the following claims.

What is claimed is:

1. Apparatus capable of one or more of pumping, filtering, oxygenating and degassing a fluid, comprising:
    a plurality of stackable support members assembled to form one or more of a pumping module, filtering module, oxygenating module and debubbling module; and
    wherein each module has a connector and selectively connects to at least one other module having a different function selected from the group consisting of pumping, filtering, oxgenating and debubbling.

2. The apparatus of claim 1, wherein the support members are similarly-shaped.

3. The apparatus of claim 2, wherein the support members are plate-shaped.

4. The apparatus of claim 1, wherein the modules comprise a filtration module, an oxygenation module and a debubbler module selectively connectable in different arrangements of modules.

5. The apparatus of claim 4, wherein the modules further comprise one or more pump modules.

6. The apparatus of claim 5, wherein the filtration module comprises a filtration membrane and a degassing membrane interposed between a plurality of support members, at least one of the support members of the filtration module having a domed-out fluid cavity; the oxygenation module comprises a degassing membrane, a filtration membrane and an oxygenation membrane interposed between a plurality of support members, at least one of the support members of the oxygenation module having a domed out fluid cavity; and the debubbler module comprises a filtration, membrane and a degassing membrane interposed between a plurality of support members, at least one of the support members of the debubbler module having a domed out fluid cavity.

7. The apparatus of claim 1, wherein the modules comprise a filtration module, the filtration module comprising a filtration membrane and a degassing membrane interposed between support members, at least one of the support members of the filtration module having a domed-out fluid cavity.

8. The apparatus of claim 7, wherein the filtration membrane of the filtration module is formed of a macro-reticular hydrophobic polymer and the degassing membrane is formed of a macro-reticular degassing membrane with a reverse flow aqueous pressure differential of at least 100 mmHg for $CO_2$ removal.

9. The apparatus of claim 7, wherein the support members of the filtration module further include a support member with a cut out center, on either side of which are disposed the filtration membrane and the degassing membrane, and a solid support member, the support member with a cut out center being disposed on one side of the at least one support member having a domed-out fluid cavity and the solid support member being disposed on another side of the at least one support member having a domed-out fluid cavity, and the filtration module further includes a first outlet for the passage of fluid to an adjacent module and a second outlet through which a vacuum is applied to draw gas out of fluid passing along the degassing membrane.

10. The apparatus of claim 1, wherein the modules comprise an oxygenation module, the oxygenation module comprising a degassing membrane, a filtration membrane and an oxygenation membrane interposed between support members, at least one of the support members of the oxygenation module having a domed out fluid cavity.

11. The apparatus of claim 10, wherein the degassing membrane of the oxygenation module is a formed of a macro-reticular degassing membrane with a reverse flow aqueous pressure differential of at least 100 mmHg, the filtration membrane of the oxygenation module is formed of a macro-reticular membrane, and the oxygenation membrane of the oxygenation module is formed of a macro-reticular oxygenation membrane with a reverse flow aqueous pressure differential of at least 100 mmHg.

12. The apparatus of claim 10, wherein the at least one support member of the oxygenation module having a domed-out fluid cavity comprises two support members having a domed-out fluid cavity, one of the two support members including an inlet for receiving oxygen therein from an external source and the other of the two support members including an outlet for the passage of fluid to an adjacent module, and wherein the support members of the oxygenation module further include a support member with a cut out center, on either side of which are disposed the filtration membrane and the oxygenation membrane, and a solid support member, the support member with a cut out center being disposed between the two support members having a domed-out fluid cavity, the solid support member being disposed on another side of the one of the two support members having a domed-out fluid cavity, and the degassing membrane being disposed on another side of the other of the two support members having a domed-out fluid cavity.

13. The apparatus of claim 1, wherein the modules comprise a debubbler module, the debubbler module comprising a filtration membrane and a degassing membrane interposed between support members, at least one of the support members of the debubbler module having a domed out fluid cavity.

14. The apparatus of claim 13, wherein the filtration membrane of the degassing module is formed of a macro-reticular filtration membrane and the degassing membrane of the degassing module is formed of a macro-reticular degassing membrane with a reverse flow aqueous pressure differential of at least 100 mmHg.

15. The apparatus of claim 13, wherein the at least one support member of the debubbler module having a domed-out fluid cavity comprises two support members having a domed-out fluid cavity, one of the two support members including a first outlet that is applied to draw gas out of fluid passing along the degassing membrane and the other of the two support members including a second outlet for the passage of fluid to an adjacent module, and wherein the debubbler module further includes a support member with a cut out center, on either side of which are disposed the filtration membrane and the degassing membrane, the support member with a cut out center being disposed between the two support members having a domed-out fluid cavity.

16. The apparatus of claim 1, wherein the modules comprise at least one pump module.

17. The apparatus of claim 16, wherein the at least one pump module comprises a plurality of support members and a diaphragm interposed between the support members, at least one of the support members having a domed out fluid cavity.

18. The apparatus of claim 16, wherein the at least one of the support members of said pump module having a domed out fluid cavity comprises two support members having a domed out fluid cavity, one of the two support members including an inlet for receiving pump fluid therein from an external source and the other of the two support members including an inlet for receiving fluid therein, and wherein the pump module further comprises a support member with a cut out center, the support member with a cut out center being disposed between the two support members having a domed-out fluid cavity, the diaphragm being interposed between the support member with a cut out center and the other of the two support members.

19. The apparatus of claim 1, wherein at least one of the modules includes a sensor port.

20. The apparatus of claim 1, further comprising means for releasably connecting the support members together without damage.

21. A method of making an apparatus for pumping, filtering, oxygenating and/or degassing a fluid, comprising:
assembling a plurality of stackable support members to form one or more of a pumping module, filtering module, oxygenating module and debubbling module; and
assembling at least two modules together each module having a different function selected from the group consisting of pumping filtering oxygenating and debubbling.

22. The method of claim 21, wherein the modules comprise a filtration module, an oxygenation module and a debubbler module and the method includes selectively arranging the modules during assembly.

23. A method for pumping, filtering, oxygenating and/or degassing a fluid, comprising:
flowing a fluid through a plurality of modules, each module formed of a plurality of stackable support members, and each module capable of one of pumping, filtering, oxygenating and debubbling a fluid wherein the modules comprise a filtration module, an oxygenation module and a debubbler module.

24. The method of claim 23, wherein the fluid is blood.

25. The method of claim 24, wherein the flowing step is performed on a patient in the field.

26. The method of claim 23, wherein the modules further comprise one or more pump modules.

* * * * *